United States Patent [19]
Hjertman

[11] Patent Number: 5,549,561
[45] Date of Patent: Aug. 27, 1996

[54] INJECTION CARTRIDGE ARRANGEMENT

[75] Inventor: Birger Hjertman, Vällingby, Sweden

[73] Assignee: Pharmacia AB, Sweden

[21] Appl. No.: 325,208

[22] PCT Filed: Apr. 16, 1993

[86] PCT No.: PCT/SE93/00335

§ 371 Date: Nov. 25, 1994

§ 102(e) Date: Nov. 25, 1994

[87] PCT Pub. No.: WO93/20867

PCT Pub. Date: Oct. 28, 1993

[30] Foreign Application Priority Data

Apr. 21, 1992 [SE] Sweden .................................. 9201246

[51] Int. Cl.[6] .......................... A61M 5/145; A61M 5/19
[52] U.S. Cl. .......................... 604/131; 604/416; 604/148; 604/191; 222/136
[58] Field of Search .................... 604/131, 134, 604/135, 148, 416, 191; 222/136, 129

[56] References Cited

U.S. PATENT DOCUMENTS 2,591,046   3/1948   Brown ........................................ 128/218

FOREIGN PATENT DOCUMENTS

0298067A1   12/1989   European Pat. Off. .
0511402A1   2/1992    European Pat. Off. .
WO92/08504  7/1992    WIPO .

Primary Examiner—John G. Weiss
Attorney, Agent, or Firm—Pollock, Vande Sande & Priddy

[57] ABSTRACT

An injection cartridge of the dual-chamber type and containing a solid product in a front chamber and a liquid product in a rear chamber further contains in the front chamber a medium that is soluble in the liquid product, and which preferably is a soluble gas. By this arrangement, the formation of gas bubbles is minimized when the solid and liquid products are mixed.

20 Claims, 2 Drawing Sheets

INJECTION CARTRIDGE ARRANGEMENT

BACKGROUND OF THE INVENTION

The present invention relates to the field of injection cartridges, and more specifically to injection cartridges of the dual-chamber type. The invention also relates to a method for manufacturing such injection cartridges.

In the field of hypodermic injections, injection cartridges have found a wide use. Such cartridges are provided prefilled with a liquid composition to be injected and are usually provided with a movable piston-like wall at one end and a wall which can readily be pierced by an injection needle or cannula at the other end. When an injection is to be administered, the user inserts the cartridge into the barrel of a syringe adapted to receive the cartridge, and a liquid connection with the contents of the cartridge is established by an injection needle through the aforementioned piercable wall. By applying pressure on the other, movable wall, the liquid is then forced out through the needle and may be administered to a patient.

Such injection cartridges have a number of important advantages. As they are supplied to the user in a prefilled state, there is no need to fill the syringe by drawing liquid up through the needle from a storage bottle containing the composition to be injected. This of course gives a much improved security against contamination from bacteria and small particles which may be released when the closure of the storage bottle is pierced. Furthermore, by the use of suitable injection devices, the injection from cartridges can be simplified so much that the patient can carry out the injection on himself. This is of great importance, for example to persons suffering from diabetes, who have to take frequent injections of insuling.

A further development of the injection cartridges has been the dual-chamber cartridges. Such cartridges are used when the substance to be injected is not stable in solution, but has to be stored in the form of a dry powder, which is dissolved or dispersed in a liquid phase immediately before administering to a patient. Such cartridges have a movable, piston-like wall at one end and a piercable wall at the other end like those cartridges described in the foregoing, but are additionally provided with a second movable, piston-like wall inside the barrel of the cartridge between its two ends, and also with a bypass channel, which is usually arranged in the wall of the cartridge. Thus, the second movable wall divides the cartridge internally into two chambers one of which containing the dry injection substance and the other containing the liquid phase to be mixed with said dry substance. The liquid phase is usually water or an aqueous liquid. Immediately before administering, the liquid is caused to flow through the bypass channel into the chamber containing the solid substance so that said substance is dissolved or dispersed in the liquid phase. This solution or dispersion may then be injected into a patient. The function of a dual-chamber cartridge will be described in more detail in the following specification.

These dual-chamber injection cartridges have all the advantages mentioned for the single-chamber cartridges above, and in addition provide an added security against the injection substance being degraded when it is in a state of solution or dispersion in a liquid phase. However, they still have a number of shortcomings, which make certain improvements desirable:

The solid substance in the front chamber of a dual-chamber injection cartridge is usually surrounded by a gaseous phase, which is usually air. This means that when the liquid phase is made to flow from the rear chamber through the bypass channel into the front chamber to be mixed with the solid substance, air bubbles will be formed and will adhere to the internal wall of the cartridge. The problem is aggravated by the fact that said internal wall has usually been made hydrophobic to facilitate the movement of the movable walls. The frequency, amount and size of such air bubbles formed are dependent on a number of factors, such as the wetting characteristics between the liquid and the internal wall of the cartridge, the material of the cartridge, and other factors. In all cases, however, the air bubbles formed are very difficult to remove.

The presence of air bubbles in the preparation to be injected is highly undesirable. The most important problem is that if air bubbles above a certain critical size are injected, they may block the capillary blood vessels and give rise to very serious consequences. However, the air bubbles are undesirable even if their size is below the critical value, and even if they are not injected at all. As the air bubbles are compressible, this leads to a decreased accuracy in the dosing of the preparation. Furthermore, due to the magnifying-glass effect of the liquid in the cartridge, the small air bubbles adhering to the internal wall will look much bigger, and this gives rise to anxiety in the user, who is usually aware of the risks associated with the presence of big air bubbles in a preparation for injection.

It is therefore an object of the present invention to provide an injection cartridge of the dual-chamber type wherein the disadvantages mentioned in the foregoing are eliminated. This object is achieved through the present invention.

SUMMARY OF THE INVENTION

According to the invention, an injection cartridge of the dual-chamber type is provided, which comprises a front chamber which contains a solid product, and a rear chamber which contains a liquid product, said front and rear chambers being separated by a fluid-sealing movable wall, and a bypass channel for conducting the liquid product from said rear chamber into said front chamber to be mixed with the solid product to form a preparation to be injected. What characterizes the cartridge of the invention is that the solid product in the front chamber is surrounded by a medium which is soluble in the liquid product.

In a preferred embodiment, the liquid product is water or an aqueous liquid, such as a solution or dispersion.

In a further preferred embodiment, the soluble medium surrounding the solid product in the front chamber is a gas which is soluble in the liquid product. A preferred gas is carbon dioxide.

In a still further preferred embodiment, the cartridge is provided with means to maintain a substantially constant pressure in the front chamber. Preferrably, these means comprise a further movable, fluid-sealing wall arranged immediately in front of the solid product.

The invention also relates to a method for the manufacture of an injection cartridge of the dual-chamber type in accordance with the foregoing. What characterizes this method is that at the filling of the cartridge, the solid product in the front chamber is surrounded by a medium which is soluble in the liquid product which is filled into the rear chamber. Preferrably, this medium is a gas which is soluble in said liquid product.

In a preferred embodiment of this method, the solid product is prepared by freeze-drying a solution of said solid product directly in the front chamber of the cartridge, and introducing the soluble gas into the front chamber after said freeze-drying, and subsequently sealing said front chamber.

DESCRIPTION OF PREFERRED AND VARIOUS EMBODIMENTS

The invention will now be described in more detail, with reference to the accompanying drawings.

Figure 1:
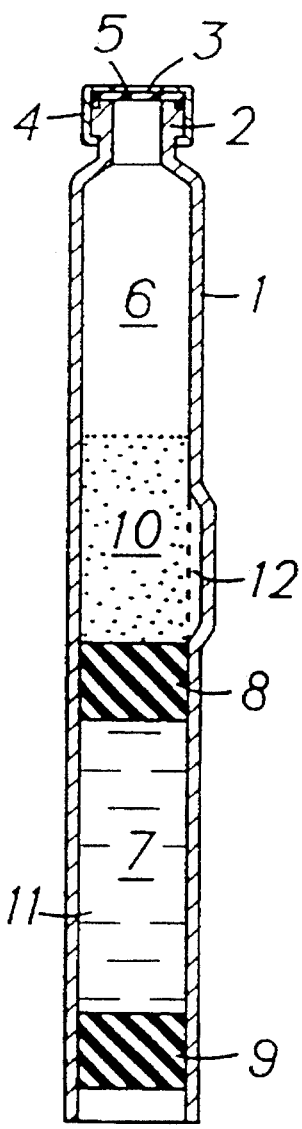
FIG. 1 shows an injection cartridge of the dual-chamber type according to the invention.

FIG. 1 shows a longitudinal sectional view of a dual-chamber injection cartridge according to the invention. The cartridge comprises a barrel 1, which is usually shaped as a circular hollow cylinder. At its front end, the barrel is shaped as a bottle-neck and has a flange 2. The front end is sealed by a septum or membrane 3 of rubber or plastic material, which is to be pierced by an injection needle or cannula, and a metal or plastic capsule 4 which is secured around the flange 2 to hold the septum 3 in sealing connection with the front end of the cartridge. The septum 3 is exposed through a central opening 5 in the capsule 4.

The cartridge is divided into a front chamber 6 and a rear chamber 7, which are separated by an intermediate, fluid-sealing movable wall 8. This wall 8 thus has the function of a piston. The rear chamber 7 is closed off to the atmosphere by a rear, fluid-sealing movable wall 9, which also serves as a piston.

In the front chamber 6 of the cartridge a solid product 10 is provided, which is usually in the form of a powder. This product is to be dissolved by or dispersed in a liquid product 11, which is provided in the rear chamber 7 of the cartridge. For conducting the liquid product 11 from the rear chamber 7 into the front chamber 6, a bypass channel 12 is arranged in the wall of the cartridge barrel 1.

When the composition to be administered is to be prepared, pressure is applied on the rear movable wall 9 to urge it forward. As the rear chamber is essentially completely filled with liquid, which is substantially incompressible, the intermediate movable wall 8 will also be urged forward, up to a position when it is just across the bypass channel 12. The liquid will then, by further pressure on the rear wall 9, flow through the bypass channel 12 into the front chamber 6, to be mixed with the solid product 10. When all the liquid has passed over into the front chamber 6, the rear wall 9 will also be in direct contact with the intermediate wall 8, and the two walls will act as one single piston when the mixture of solid and liquid products is to be injected through an injection needle or cannula (not shown in the drawing) which has been inserted through the septum 3.

In the cartridge shown in FIG. 1, it is necessary that there is an empty space in the front chamber 6 to receive the liquid 11 from the rear chamber 7. According to the prior art, this empty space usually contains air at atmospheric pressure, which also surrounds the individual particles of the solid product. This also means that the pressure in the front chamber will rise when the essentially incompressible liquid 11 is introduced into said front chamber. When the solid and the liquid products are mixed to form a solution or dispersion, the air will remain as a separate gaseous phase in the form of bubbles of varying size. As has been explained in the foregoing, these bubbles are highly undesirable, regardless of whether they accompany the liquid when it is injected or remain in the front chamber of the cartridge.

However, when, in accordance with the present invention, the air in the space of the front chamber 6 is replaced with a medium which is soluble in the liquid product. Thus, when the liquid 11 is introduced into the front chamber 6, it will form an assentially homogenous phase with the medium, and no air bubbles will be formed. The medium may be a liquid, but is preferably a gas which is soluble in the liquid product.

As a gaseous medium which is soluble in the liquid product, which is usually water or an aqueous liquid, carbon dioxide is suitable. One volume of carbon dioxide will dissolve in about one volume of water at atmospheric pressure and normal room temperature. Other gases may also be possible, such as ammonia, especially when the liquid product is an ammonium ion buffer. The choice of medium also dependent on the desired pH value in the final preparation to be injected.

It goes without saying that the soluble medium selected must be one which does not exert any harmful influence on the preparation to be injected or when it itself is injected into the body. In the very small amounts that are injected, it has been found that carbon dioxide is essentially free from harmful side effects.

In the front chamber, the amount of gas should be as low as possible, as this decreases the solubility requirements. This means that the empty space in the front chamber should be as small as possible, so that the risk that bubbles are formed will be decreased. However, this works against the requirement that there must be sufficient room for the liquid product which is to be mixed with the solid product. A smaller space will also lead to a higher pressure in the front chamber when the liquid is introduced. This is undesirable, as more gas will be dissolved in the liquid at the higher pressure, but will be liberated again when the pressure is released, as occurs when the preparation is injected. However, through an embodiment of the cartridge of the present invention, this problem is eliminated.

Thus, in a preferred embodiment of the invention, the cartridge is provided with means for relieving any superatmospheric pressure formed and maintain a substantially constant pressure in the front chamber at the mixing of the solid product with the liquid product. These means may be of different designs, and may, for example, consist of valve arrangements of various types. In the most preferred embodiment, however, a third, fluid-sealing movable wall is arranged in the front chamber immediately in front of the solid product.

Figure 2:
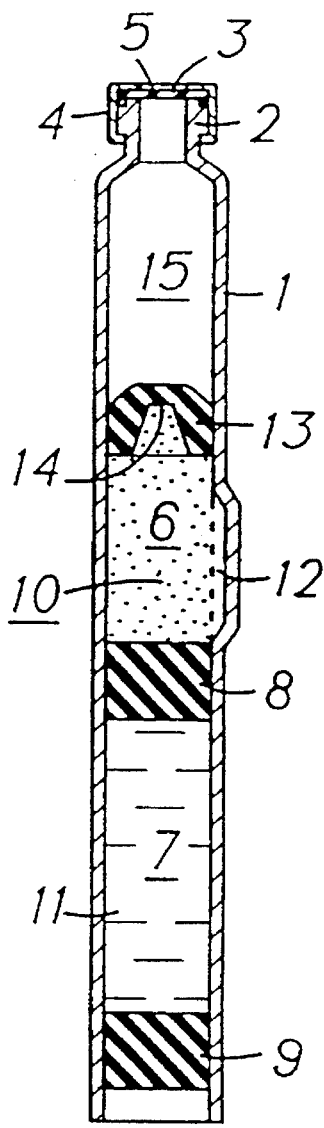
FIG. 2 shows a preferred embodiment of an cartridge of the invention, having a further movable wall in front of the solid product.

This embodiment is shown in FIG. 2 of the drawing. In this figure, features which are identical with those in FIG. 1 have the same reference numbers.

In the same way as shown in FIG. 1, the cartridge comprises a barrel 1, which is shaped like a bottleneck at its front end and has a flange 2. The front end is sealed by a septum 3 and a capsule 4, which is secured around the flange 2.

Internally, the cartridge is divided into a front chamber 6 and a rear chamber 7, which are separated by an intermediate, fluid-sealing, movable wall 8, and the rear chamber 7 is closed at its rear end by a rear, fluid-sealing, movable wall 9. A solid product 10 is provided in the front chamber 6, and a liquid product 11 is provided in the rear chamber 7. There is also a bypass channel 12 arranged between the front chamber and the rear chamber.

In accordance with the invention, the front chamber 6 also contains a medium which is soluble in the liquid product 11, preferably then a soluble gas, such as carbon dioxide.

However, in accordance with a preferred embodiment of the invention, a third, fluid-sealing movable wall 13 is arranged in the front chamber 6 immediately in front of the solid product 10. This front movable wall 13 is arranged close to the solid product 10 such that it compresses the solid product more or less strongly and in this way minimizes the space that is occupied by the product. As a consequence, the amount of soluble medium is also minimized, which makes it easier to dissolve in the liquid medium.

The front movable wall 13 is preferably provided with a depression at its center, as is shown at 14, such that it is made thinner at its central part. This will facilitate the penetration of an injection needle or cannula.

The forward-facing side of the front movable wall 13 may also be shaped to conform with the interior of the forward end of the cartridge, as shown in the figure. In this way, the dead space in front of said movable wall is minimized when the wall is in its foremost position.

Through the arrangement of the front movable wall 13 in close contact with the solid product 10, there will be provided an empty space 15 in front of the front movable wall 13. This space 15 will usually contain air or some other gas, and to prevent the build-up of a superatmospheric pressure when the front movable wall 13 is moved forwards, means should be arranged for relieving the pressure in the space 15. Such means may be arranged as various types of valves (not shown in the figure), or by simply inserting the injection needle through the septum 3 before the front movable wall is moved forwards, so that a connection with the outside atmosphere is established.

When the composition to be injected is to be prepared, pressure is applied on the rear movable wall 9 to urge it forwards. As the liquid product 11 in the rear chamber 7 is substantially incompressible, the pressure will also urge the intermediary movable wall 8 forwards. This intermediary movable wall 8 will in turn act on the compressed solid product 10, so that it will push the front movable wall 13 forwards. When the intermediate wall 8 has reached a position alongside the bypass channel 12, further pressure on the rear wall 9 will urge the liquid product 11 through said channel into the front chamber 6 to be mixed with the solid product 10 and dissolve it or disperse it in the liquid phase, which is usually an aqueous phase. At this stage, the intermediate wall 8 will not move any further forwards, but the pressure transmitted by the liquid flowing through the bypass channel 12 into the front chamber 6 will cause the front movable wall 13 to move forwards, so that no superatmospheric pressure is built up in the front chamber 6.

As the liquid flows into the front chamber 6, the medium surrounding the particles of the solid product 10 dissolves in the liquid, so that no gas bubbles are formed in the resulting solution or dispersion of the solid product in the liquid. The solid product being more or less compressed by the front movable wall 13, the free space around the particles of the solid product is kept to a minimum, which also minimizes the amount of medium to be dissolved in the liquid. At the same time, no superatmospheric pressure is built up in the front chamber 6, and the dissolution properties of the medium in the liquid are not affected.

During the movement of the front movable wall forwards, there has been no build-up of an overpressure in the space 15 in front of said wall, as this space is in a pressure-relieving connection with the outer atmosphere, for example through some kind of valve arrangement, or through an injection needle inserted through the septum 3. Thus, the movement of the front wall is not disturbed by any counter-pressure, and this is of importance when very sensitive substances are to be dissolved in a liquid phase for subsequent injection.

When all the liquid has been transferred into the front chamber 6 and the solid product 10 has been completely dissolved or dispersed in the liquid product, the cartridge is ready for injection. An injection needle or cannula (not shown in the drawing) is inserted through the septum 3 and the thin part 14 of the front movable wall 13, so that a liquid connection with the outside is established. In a variant, the needle has previously been inserted through the septum 3, and will then penetrate the front movable wall 13 as said wall is pushed to its foremost position. It goes without saying that the capacities of the rear chamber 7, the front chamber 6 and the space 15 should be adapted to each other in such a way that there will be sufficient room in the front chamber for the solution or dispersion of the solid product 10 and the soluble medium in the liquid product 11 when all the liquid has been transferred from the rear chamber 7 into the front chamber 6, and the front movable wall 13 is in its foremost position. This foremost position should then also be close to the front end of the cartridge, so that the injection needle or cannula can easily be inserted through the septum 3 and the front movable wall 13.

In another embodiment of the cartridge of the invention, the front movable wall 13 in FIG. 2 can be dispensed with, and there is only a valve arrangement at the front end of the cartridge, or the injection needle is inserted through the septum 3 immediately before the injectable composition is prepared. In this way, there will be no build-up of an overpressure as the liquid product 11 is transferred into the front chamber 6, but the amount of soluble medium used in accordance with the invention will not be minimized. Also, there is a risk that some of this medium will be lost to the atmosphere, especially if it is a gas, and that there will be an increased risk of contamination from the outer atmosphere. Therefore, this embodiment, although it will work, is less preferred.

When the cartridge is to be used for the preparation of the injectable composition and its subsequent administration, it is usually placed in a suitable holder, for example of the syringe type. Such a holder is generally provided with means for exerting pressure on the rear movable wall and subsequent injection, such as a plunger, which may be actuated manually or mechanically. The holder is also provided with means at its front end for connecting the cartridge with an injection needle or cannula. This connection may be an injection needle which is pointed at both its ends for a direct injection from the cartridge, or it may include a tube, which at its other end is connected with an injection needle for administering the composition to the patient. Holders of this type are well-known to those skilled in the art, and do not have to be modified in any way for the practice of the present invention. This is a further advantage of the invention.

The injection cartridges of the invention are manufactured by processes similar to those previously known for the manufacture of prior art injection cartridges of the dual-chamber type. However, the characteristic feature of the method of the present invention is that at the filling of the cartridge, the solid product which is filled into the front chamber of the cartridge is surrounded by a medium which is soluble in the liquid product which is filled in the rear chamber of the cartridge. This can be arranged in different ways. One method is to inject the medium into the front chamber before said chamber is closed at its front or rear end. Another, preferred method can be used when the solid product is filled into the cartridge in the form of a solution, which is then freeze-dried in place directly in the front chamber. In this case, the medium is gaseous, and is introduced into the freeze-drying chamber before the vacuum in said chamber is released. The front chamber with the freeze-dried product should then preferably be sealed while it is still in the freeze-drying chamber, and a method and a special sealing device for this will be described in more detail below.

If the cartridge is to contain a third movable wall, as shown in FIG. 2, this wall may be inserted into the barrel of the cartridge before it is filled with the solid product. In another variant, the cartridge does not have a front end like a bottleneck, but has straight sides, so that the third wall may be inserted from the front end after the solid product has been filled into the front chamber. The modifications necessary for the different variants may easily be worked out by a person skilled in the art.

As stated above, a preferred method for manufacturing the cartridges of the invention is to freeze-dry the solid product in the front chamber directly, while this chamber has not yet been sealed, and subsequently introduce a gaseous soluble medium and then seal the cartridges while they are still in the freeze-drying apparatus. This embodiment is described in more detail with reference to FIGS. 3A and 3B of the drawing.

Figure 3A:
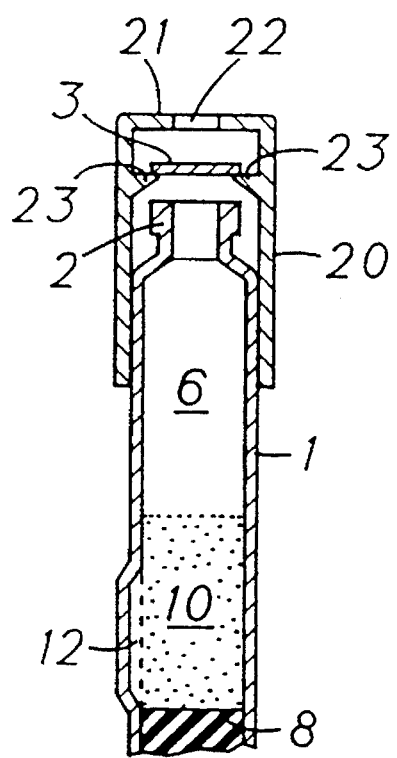
FIGS. 3A and 3B show a capsule arrangement for sealing the cartridge after freeze-drying of the solid product and introduction of the soluble medium.
Figure 3B:
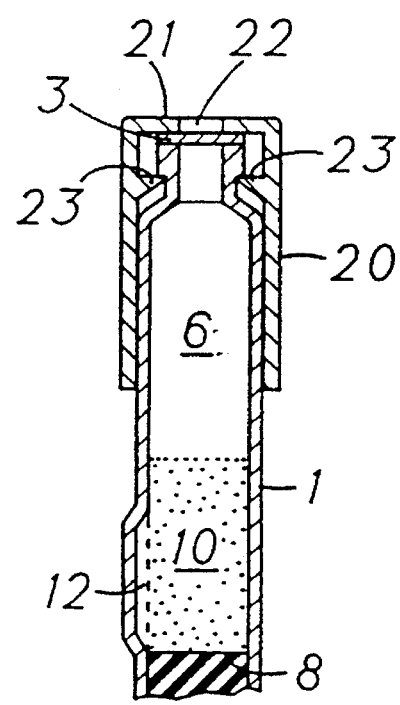

FIGS. 3A and 3B show a longitudinal sectional view of the front part of an injection cartridge of the invention before and after sealing, respectively. Features which are the same as those shown in FIGS. 1 and 2 have the same reference numbers as in those figures.

The figures show the front part of an injection cartridge like the one described under FIG. 1. Thus, the cartridge comprises a barrel 1 with the front chamber 6 and the intermediate movable wall 8 and the bypass channel 12 in the wall of the cartridge. The front chamber contains the solid product 10, which has been obtained by freeze-drying a solution of said product directly in the front chamber. As the front end of the cartridge is not yet closed, water vapor can escape through the opening in said front end, so that the freeze-drying becomes possible.

The front end of the cartridge is bottle-shaped and has a flange 2 around the outside of its neck. A septum 3 of rubber or plastic material is arranged to be pressed against the flanged neck of the cartridge, so that a complete seal is assured. The septum can be penetrated by an injection needle or cannula (not shown) when an injection is to be administered from the cartridge.

The cartridge is closed by a capsule which comprises a sleeve portion 20 which fits over the barrel 1 of the cartridge. At its upper end, the sleeve is closed by an end wall 21, which has a central opening 22.

On its interior wall, the sleeve 20 of the capsule is provided with lugs 23. These lugs are arranged to be resilient, so that they may be slid over the flange 2, but will then snap out to secure the capsule against the rear edge of the flange 2. A number of lugs 23 are arranged around the inner circumference of the sleeve 1, so that the capsule will be held securely in place.

The septum 3 is arranged above the lugs in such a way that it will be secured against the front surface of the flange 2 when the capsule is secured to the cartridge by means of the lugs 23 against the rear edge of the flange 2. For this, the septum 3 may rest against the upper edges of the lugs, as shown in FIG. 3A, or it may be attached to the underside of the end wall 21, so that it already covers the central opening 22. Other arrangements are also possible. What is important is that the septum should securely seal the opening in the cartridge when the capsule has been secured in place, and that before the sealing, there should be a fluid connection possible between the inside of the front chamber 6 of the cartridge and the outside of the cartridge and the capsule, so that the freeze-drying and subsequent introduction of the soluble gaseous medium will be possible.

FIG. 3B shows how the capsule has been secured to the cartridge to seal it against the outside. The sleeve 20 has been slid down the barrel 1 of the cartridge such that the lugs 23 have passed over the flange 2 on the neck of the cartridge and are now resting against the rear edge of said flange. The inside of the front wall 21 now rests against the septum 3 and presses it securely against the front surface of the flange 2. It is clear that the distance between the upper edges of the lugs 23 and the inside of the front wall 21 should be adapted to the thicknesses of the flange 2 and the septum 3 in such a way that the septum is pressed securely against the front end of the flange 2 by the action of the resiliency of the capsule material. This resiliency is most suitably achieved through an appropriate selection of a suitable plastic material for the capsule.

When the capsule is now secured in place, the septum 3 is exposed through the central opening 22 in the end wall 21. This makes it possible to insert an injection needle or cannula through the septum for the administering of the injectable preparation from the cartridge.

The closing of the cartridges after the freeze-drying and the introduction of gaseous soluble medium may be carried out by the use of equipment which is known to those skilled in the art. Thus, the cartridges containing the solution which is to be freeze-dried may be secured in an upright position on trays, and the capsules may be mounted facing downwards in a similar arrangement on other trays. The two trays may then be brought together such that the sleeves 20 of the capsules will engage the barrels 1 of the cartridges, but will not yet seal the cartridges, as is shown in FIG. 3A. This assembly of cartridges and capsules is then introduced into the freeze-drying apparatus, and the freeze-drying process is carried out in a conventional manner. After this process has been completed, the gaseous soluble medium is introduced into the apparatus before the vacuum is released. In this way, said gaseous soluble medium will quickly and easily penetrate into the interior of the cartridges to surround the freeze-dried solid product. Thereafter, the two trays are brought further together by some suitable mechanical or electro-mechanical arrangement, such that the lugs 23 in the capsules are passed over the flanges of the cartridges and snap in to be secured against the rear edges of said flanges. The cartridges are now sealed against the outside atmosphere and contamination from the outside, and may be removed from the freeze-drying apparatus.

The choice of materials for the various parts of the cartridges and capsules of the invention does not present any difficulties for a person skilled in the art. Depending on the specific pharmaceutical agents used, various types of glass, plastic materials and metal may be contemplated. It is of course important that the materials selected are completely acceptable from a pharmaceutical point of view and do now have any harmful effect on the preparations to be used. Also, the materials must be easy to sterilize, so that security against contamination is achieved.

Furthermore, it is clear that all the processes for the manufacture of the cartridges of the invention must be carried out with the observation of strict pharmaceutical practice, so that no contamination is introduced. This is self-evident to those skilled in the art, and conventional practice can be followed.

In the foregoing, the present invention has been described with the reference to embodiments shown in the drawing. The person skilled in the art will understand, however, that these embodiments are only examples and do not serve to restrict the scope of the invention in any way.

I claim:

1. An injection cartridge of the dual-chamber type, comprising a front chamber which contains a solid product, and a rear chamber which contains a liquid product, said front and rear chambers being separated by a fluid-sealing movable wall, and a bypass channel for conducting the liquid product from said rear chamber into said front chamber to be mixed with the solid product to form a preparation to be injected, characterized in that the solid product in the front chamber is surrounded by a medium which is soluble in the liquid product.

2. An injection cartridge according to claim 1, characterized in that the liquid product is water or an aqueous liquid.

3. An injection cartridge according to claim 2, characterized in that the medium surrounding the solid product is a gas which is soluble in the liquid product.

4. An injection cartridge according to claim 2, characterized in that said cartridge is provided with means to maintain a substantially constant pressure in the front chamber.

5. An injection cartridge according to claim 1, characterized in that the medium surrounding the solid product is a gas which is soluble in the liquid product.

6. An injection cartridge according to claim 5, characterized in that said cartridge is provided with means to maintain a substantially constant pressure in the front chamber.

7. An injection cartridge according to claim 5, characterized in that the medium is carbon dioxide.

8. An injection cartridge according to claim 7, characterized in that said cartridge is provided with means to maintain a substantially constant pressure in the front chamber.

9. An injection cartridge according to claim 1, characterized in that said cartridge is provided with means to maintain a substantially constant pressure in the front chamber.

10. An injection cartridge according to claim 9, characterized in that a further fluid-sealing movable wall is arranged in the front chamber immediately in front of the solid product.

11. An injection cartridge according to claim 9, characterized in that said front chamber is provided with outlet means for the outflow of the medium when the liquid product is mixed with the solid product.

12. A method for the manufacture of an injection cartridge according to claims 1, characterized in that when a front chamber of the cartridge is filled with the solid product, said product is surrounded by a medium which is soluble in a liquid product which is filled in the rear chamber of the cartridge.

13. A method according to claim 12, characterized in that said medium is a gas which is soluble in said liquid product.

14. The method according to claim 13, characterized in that said solid product is prepared by freeze-drying a solution of the solid product directly in said front chamber of the cartridge, and introduction of said soluble gas into the front chamber after the freeze-drying.

15. A method for the manufacture of an injection cartridge according to claim 2, characterized in that when a front chamber of the cartridge is filled with the solid product, said product is surrounded by a medium which is soluble in a liquid product which is filled in the rear chamber of the cartridge.

16. A method for the manufacture of an injection cartridge according to claim 5, characterized in that when a front chamber of the cartridge is filled with the solid product, said product is surrounded by a medium which is soluble in a liquid product which is filled in the rear chamber of the cartridge.

17. A method for the manufacture of an injection cartridge according to claim 7, characterized in that when a front chamber of the cartridge is filled with the solid product, said product is surrounded by a medium which is soluble in a liquid product which is filled in the rear chamber of the cartridge.

18. A method for the manufacture of an injection cartridge according to claim 9, characterized in that when a front chamber of the cartridge is filled with the solid product, said product is surrounded by a medium which is soluble in a liquid product which is filled in the rear chamber of the cartridge.

19. A method for the manufacture of an injection cartridge according to claim 10, characterized in that when a front chamber of the cartridge is filled with the solid product, said product is surrounded by a medium which is soluble in a liquid product which is filled in the rear chamber of the cartridge.

20. A method for the manufacture of an injection cartridge according to claim 11, characterized in that when a front chamber of the cartridge is filled with the solid product, said product is surrounded by a medium which is soluble in a liquid product which is filled in the rear chamber of the cartridge.

* * * * *